United States Patent [19]

Erdős et al.

[11] Patent Number: 5,108,757

[45] Date of Patent: Apr. 28, 1992

[54] SOLID PHARMACEUTICAL COMPOSITION AND A PROCESS FOR PREPARING SAME

[75] Inventors: Sándor Erdős; József Kenderfi; Erzsébet Bárczay; Aranka Hegedüs née Szima; Mária Krisztián; Attila Mándi; Éva Tajthy née Juhasz; Péter Tömpe; Margit Csörgő; Márton Fekete; Frigyes Görgényi; Zoltán Torma, all of Budapest, Hungary

[73] Assignee: EGIS Gyogyszergyar, Hungary

[21] Appl. No.: 493,283

[22] Filed: Mar. 14, 1990

[30] Foreign Application Priority Data

Mar. 14, 1989 [HU] Hungary .............................. 1215/89

[51] Int. Cl.$^5$ .............................................. A61K 9/48
[52] U.S. Cl. ..................................... 424/451; 424/452; 424/482; 424/499
[58] Field of Search .................. 424/78, 499, 452, 482

[56] References Cited

U.S. PATENT DOCUMENTS

| | | | |
|---|---|---|---|
| 4,673,564 | 6/1987 | Kawata | 424/78 |
| 4,828,836 | 5/1989 | Elger | 424/499 |
| 4,894,235 | 1/1990 | Köhne | 424/452 |
| 4,968,508 | 11/1990 | Oren | 424/482 |

*Primary Examiner*—Thurman K. Page
*Assistant Examiner*—William E. Benston
*Attorney, Agent, or Firm*—Ostrolenk, Faber, Gerb & Soffen

[57] ABSTRACT

The present invention relates to a process for the preparation of regulated release solid pharmaceutical compositions comprising 4-(2'-nitro-phenyl)-2,6-dimethyl-3,5-dimethoxycarbonyl-1,4-dihydro-pyridine (referred to further on as "nifedipine") as active ingredient which comprises admixing a solution or solutions of 1 part by weight of nifedipine, 0.1-1.5 parts by weight of one or more hydrophilizing agent(s) and 0.05-1.5 parts by weight of one or more retarding agent(s) formed with one or more identical or different solvent(s) completely or partly and applying the solution(s) thus obtained simultaneously or in succession onto an inert carrier, drying and sieving the product thus obtained and subsequently admixing the same with suitable conventional auxiliary agents and compressing the mixture thus obtained to tablets in a known manner and coating the tablets or filling the mixture into capsules.

21 Claims, No Drawings

SOLID PHARMACEUTICAL COMPOSITION AND A PROCESS FOR PREPARING SAME

This invention relates to solid pharmaceutical compositions and a process for the preparation thereof. More particularly it is concerned with regulated release solid pharmaceutical compositions comprising 4-(2'-nitro-phenyl)-2,6-dimethyl-3,5-dimethoxycarbonyl-1,4-dihydropyridine (referred to further on as "nifedipine") as active ingredient.

It is known that nifedipine is a valuable calcium antagonist and is highly useful in the treatment of high blood pressure and coronary diseases (German patent specification No. 1,620,827). The therapeutical use and formulation of nifedipine is however rendered very difficult by the low solubility and high light sensitivity of the active ingredient.

Nifedipine is used in practice in the form of fundamentally two different types of compositions.

One type of nifedipine-containing compositions is used against coronary spasm. In order to achieve the possibly quickest relief of the spasm a rapid release of the active ingredient is required which is accompanied by a sudden high blood level.

The other type of nifedipine-containing pharmaceutical compositions is applied in the prevention of coronary spasm and in treatment of high blood pressure. In this case sudden high blood level is not required but, quite on the contrary, it would be rather inconvenient because of the increased occurrence of side effects. The therapeutic effect may last from 2–3 hours to 8–10 hours, thus it encompasses compositions of relatively quick effect and those of more or less sustained (prolonged) effect.

According to DOS No. 3,033,919 the low solubility of nifedipine in water and digestive juice is improved by increasing the specific surface area to an extend that the active ingredient is released from the compositions within a therapeutically acceptable period of time. According to the process disclosed in the said patent specification the nifedipine bulk material is ground in a suitable mill, preferably a hammer mill, to a powder having a specific surface area of 0.5–6 $m^2/g$ and finishing the powder thus obtained in the form of solid pharmaceutical compositions by using suitable known carriers and auxiliary agents. Due to the character of the milling procedure the particle size of the active ingredient can be adjusted only within certain limits, and the particle size distribution of the active ingredient may vary to a significant extent even in case of a narrow particle size interval. Thus a particle size interval of about 1–10$\mu$, which corresponds to a specific surface of 0.5–6 $m^2/g$, may cause even a 2–3-fold deviation in the maximum of the density function of the particle size and this may exert an influence on the active ingredient release.

According to Hungarian patent specification No. 193,287 nifedipine-containing two-phase solid pharmaceutical compositions are prepared by dissolving nifedipine and a co-precipitant (preferably polyvinyl pyrrolidone) in an organic solvent, removing the solvent and admixing the co-precipitate thus obtained with 1–5 parts by weight, related to 1 part by weight of the nifedipine content thereof, of crystalline nifedipine having a specific surface of 1.0–6.0 $m^2/g$ and an average particle size of about 10–1$\mu$m. The drawback of this process resides in the fact that nifedipine is contained in a non-uniform granule and therefore on admixing the two different granulations segregation may take place during the tabletting and encapsulating procedure.

Calcium antagonists are more and more frequently used. For the above therapeutical purpose compositions having very precisely defined release characteristics are required, namely in the range extending from compositions which provide suddenly a high blood level through relatively quickly acting preparations to sustained release formulations. Taking into consideration the low solubility of nifedipine in water and digestive juice and also the high light sensitivity thereof, the above objects and requirements can not be solved and fulfilled by means of conventional methods.

It is the object of the present invention to elaborate a process for the simple manufacture of pharmaceutical compositions which meet the requirements of the given concrete therapeutical field.

According to an aspect of the present invention there is provided a process for the preparation of regulated release solid pharmaceutical compositions comprising 4-(2'-nitro-phenyl)-2,6-dimethyl-3,5-dimethoxycarbonyl-1,4-dihydro-pyridine (referred to further on as "nifedipine") as active ingredient which comprises admixing a solution or solutions of 1 part by weight of nifedipine, 0.1–1.5 parts by weight of one or more hydrophilising agent(s) and 0.05–1.5 parts by weight of one or more retarding agent(s) formed with one or more identical or different solvent(s) completely or partly and applying the solution(s) thus obtained simultaneously or in succession onto an inert carrier, drying and sieving the product thus obtained and subsequently admixing the same with suitable conventional auxiliary agents and compressing the mixture thus obtained to tablets in a known manner and coating the tablets or filling the mixture into capsules.

The term "relatively quick release pharmaceutical composition" used throughout the specification relates to compositions from which 50% of the active ingredient is released within a period not exceeding one hour (as determined by the method disclosed in the USP) and which, in order to reduce the side-effects on administration of one tablet or capsule, provide a maximal plasma-concentration never exceeding even temporarily the value of 80 ng/ml.

The term "sustained release pharmaceutical compositions" relates to compositions from which 50% of the active ingredient is released within a period longer than one hour.

The present invention is based on the recognition that the factors of uncertainty due to the poor solubility of nifedipine and the differences in the particle structure of the crystalline active ingredient used may be overcome by transforming nifedipine into a solution—i.e. a molecular dispersion—and applying the same onto a solid carrier together with a hydrophilising agent and a retarding agent either simultaneously or partially separately. The velocity and characteristics of the release of nifedipine may be significantly regulated by the ratio and type of the two auxiliary agents (the hydrophilising agent on the one hand and the retarding agent on the other), the ratio of nifedipine to the total amount of the said two auxiliary agents and also by the way how the solution(s) is (are) applied onto the carrier. Thus not only the speed of release but also the characteristics of the release curve may be varied.

The essence of the process of the present invention resides in the fact that nifedipine is not applied alone (per se) on the carrier but the solution of nifedipine always contains a hydrophilising and/or retarding agent or at least a part thereof.

If the hydrophilising agent or a part thereof is applied onto the carrier per se, thus must always be the last step. One has also to proceed this way if the solution of the hydrophilising agent or a part thereof contains at least partly the nifedipine, too.

The release rate of the active ingredient is completely independent of the further processing of the product, compressing to tablets, coating the same or filling into capsules. In the course of the claimed process the grinding and milling of the active ingredient is eliminated, for this reason the particle structure and particle size distribution of the starting bulk material does not play any role and consequently all the statistical fluctuations arising therefrom are overcome. According to the process of the present invention nifedipine is processed in the form of a single granulation, therefore no segregation takes place and for this reason blood level and activity remain constant within one batch and these deviations are eliminated.

It is an essential characteristic feature of the present invention that the end-product comprises nifedipine in crystalline, i.e. not in amorphous, form. Due to the presence of the other components dissolved together with nifedipine, however, these are not well-defined pure nifedipine crystals but are rather present as a coating layer on the carrier. It is, however, not intended to limit the scope of the present invention by theoretical considerations.

According to the process of the present invention preferably polyethylene glycols, hydroxypropyl cellulose, polyvidone or various surfactants (e.g. macrogol stearate Ph. Hg. VII) may be used as hydrophilising agents. One may proceed particularly preferably by using hydroxypropyl cellulose for this purpose.

As retarding agent preferably ethyl cellulose, polyvinyl acetate, polyvinyl butyrale or various types of Eudragit methacrylate copolymer (advantageously Eudragit RS) may be used. Polyvinyl butyrale proved to be particularly advantageous.

According to a particularly preferred form of realization of the process of the present invention hydroxypropyl cellulose is used as hydrophilising agent and polyvinyl butyrale is applied as retarding agent.

In order to accomplish the process of the present invention with the promised result it must be taken into consideration that the hydrophilising and retarding agents enumerated above with an illustrating but non-limiting character exert their desired effect to a different extent. Thus a smaller amount of polyvinyl butyrale is sufficient to achieve the desired retarding effect than as if Eudragit RS or ethyl cellulose were used. Similarly, the hydrophilising effect of hydroxypropyl cellulose is stronger than that of the polyethylene glycol. For this reason the ratio of the hydrophilising and retarding agents may vary between wide ranges depending on the individual components used and the extent of release to be attained.

As a general rule 0.1-1.5 parts by weight of hydrophilising agent(s) and 0.05-1.5 parts by weight of retarding agent(s) can be used, related to 1 part by weight of nifedipine.

According to an aspect of the process of the present invention relatively quick release pharmaceutical compositions may be prepared by using 0.3-1.5 parts by weight of a hydrophilising agent and 0.05-0.2 part by weight of a retarding agent, related to 1 part by weight of nifedipine.

According to an other aspect of the process of the present invention sustained release pharmaceutical compositions may be prepared by using 0.1-0.3 part by weight of a hydrophilising agent and 0.2-1.5 parts by weight of a retarding agent, related to 1 part by weight of nifedipine.

According to a particularly preferred form of realization of the process of the present invention relative quick release pharmaceutical compositions may be prepared by using 0.4 part by weight of hydroxypropyl cellulose and 0.07 part by weight of polyvinyl butyral, related to 1 part by weight of nifedipine. According to an other particularly preferred form of realization of the process of the present invention sustained release pharmaceutical compositions may be prepared by using 0.1-0.2, preferably 0.1, part by weight of hydroxypropyl cellulose and 0.3-0.5, preferably 0.45, part by weight of polyvinyl butyral, related to 1 part by weight of nifedipine.

According to the process of the present invention, the hydrophilising agent and the retarding agent are used in the form of solution(s) formed in a suitable organic solvent, preferably with a lower alkanol (particularly ethanol or isopropanol) or acetone. Ethanol proved to be particularly suitable for this purpose.

According to the process of the present invention nifedipine, the hydryphilising agent and the retarding agent may be separately dissolved in the organic solvent (preferably ethanol). The solutions thus obtained may be admixed partially in optional ratio and may be applied onto the solid carrier in succession. One may, however, also proceed by admixing the solutions of the above three components, namely nifedipine, the hydrophilising agent and the retarding agent, and applying the single solution thus obtained onto the solid carrier. One may further also proceed by dissolving the nifedipine and the hydrophilising agent(s) in ethanol and adding to the solution thus obtained the separately prepared solution of the retarding agent. According to a still further embodiment of the process of the present invention the hydrophilising agent and the retarding agent are dissolved in the organic solvent and the solution thus obtained is added to the nifedipine solution. In certain cases one may proceed preferably by applying first the solution of nifedipine, the complete amount of the retarding agent and optionally a part of the hydrophilizing agent into the carrier and subsequently spraying the solution comprising the remaining—optionally complete—amount of the hydrophilising agent onto the carrier. Nifedipine solution is, however, never applied onto the carrier alone.

The solution(s) thus obtained are applied onto the solid carrier by methods and equipments known per se by means of a known fluidization method. The solutions are sprayed onto the fluidized powder-like carrier with the aid of compressed air. Conventional kneading methods can be used as well. In the latter case the solution can be applied onto the carrier batch-wise with intermittent drying periods. One may preferably use a conventional fluidizing granulating method.

As a result of this operation the carrier being originally present in the form of a fine powder is transformed into a granular product (granules) and this facilitates further processing (tabletting, encapsulation etc.).

An inert carrier any suitable therapeutically acceptable auxiliary agent or mixtures thereof can be used, e.g. a mixture of microcrystalline cellulose and lactose in the presence or absence of a disintegrating agent (e.g., croscarmellose).

The granules prepared from the solid carrier and the solution(s) applied (sprayed) on the same are dried and sieved by any suitable method known per se whereupon they are admixed with further known auxiliary agents (e.g. talc, magnesium stearate; disintegrating agents, e.g. croscarmellose) and are compressed into tablets (preferably to convex tablets) by known methods or filled into capsules.

Because of the light sensitivity of nifedipine the tablets are preferably coated. The coating may be made of a conventional sugar type or a film. In order to protect the tablets from light it is preferred to use a coating which comprises a suitable dye or pigment. Red and/or orange dyes, red and/or orange aluminium pigments, iron oxide pigments may be used optionally together with titanium dioxide. The wall of the capsule may also advantageously comprise one or more of the above light protecting agent(s).

The advantage of the process of the present invention is that controlled (regulated) release solid nifedipine-containing pharmaceutical compositions can be prepared in a simple way readily feasible on industrial scale, too, by varying the amount and ratio of the hydrophilising agent and the retarding agent.

The process of the present invention is suitable for the preparation of both relatively quick and sustained release pharmaceutical compositions. The release of the active ingredient is independent of the pH of the medium, i.e. from the period of time during which the pharmaceutical composition stays in the stomach. According to the process of the present invention the release of the active ingredient does not depend on the particle structure of the active ingredient, either; the milling and grinding procedures accompanied by various factors of uncertainty are eliminated. Nifedipine is contained in a uniform granulation and for this reason no segregation occurs on tabletting or encapsulating.

According to a further aspect of the present invention there are provided regulated release nifedipine-containing solid pharmaceutical compositions prepared by the process as defined above.

According to a still further aspect of the present invention there are provided regulated release solid pharmaceutical compositions comprising as active ingredient nifedipine, 0.1–1,5 parts by weight of at least one hydrophilising agent and 0.05–1.5 parts by weight of at least one retarding agent(s), related to 1 part by weight of nifedipine, and optionally suitable inert conventional pharmaceutically acceptable auxiliary agents.

The relatively quick release solid pharmaceutical compositions of the present invention preferably comprise 0.3–1.5 parts by weight of a hydrophilising agent and 0.05–0.2 part by weight of a retarding agent, related to 1 part by weight of nifedipine.

The sustained release solid pharmaceutical compositions of the present invention preferably comprise 0.10–0.3 part by weight of a hydrophilising agent and 0.2–1.5 parts by weight of a retarding agent, related to 1 mole of nifedipine.

The hydrophilising agent(s), retarding agent(s) and the ratio thereof and the other components may be those as disclosed above.

Further details of the present invention are to be found in the following Examples without limiting the scope of protection to the Examples.

EXAMPLE 1

30 g of nifedipine are dissolved in 240 g of ethanol. To the solution thus obtained at first a solution of 6 g of hydroxypropyl cellulose (Klucel LF) in 50 g of ethanol, then 240 g of Eudragit RS (12.5% of Eudragit RS, 35% of acetone, 52.5% of isopropanol: C.A. Reg. No. 33,434-24-1) are added. The solution thus obtained is sprayed on a mixture of 184.5 g of microcrystalline cellulose, 84 g of lactose and 1.5 g of crospovidone (USP XXI/N.F. XVI) by means of a fluidization procedure. The mixture is sieved on a 0.9 mm sieve and then dried. Thereafter 18 g of crospovidone, 9 g of talc and 1.5 g of magnesium stearate are added. The mixture is compressed to tablets and coated or filled to capsules, respectively. According to the method of USP XXI or PhHg VII (rotating basket; 150 r.p.m.; in 900 ml of 0.1 hydrochloric acid) from the tablets thus obtained 50% of the active ingredient is released within 3 hours ($T_{50}=3$ hours).

EXAMPLE 2

35 g of nifedipine are dissolved in 280 g of ethanol. At first 280 g of an Eudragit RS 12.5 solution are added to the solution whereupon the solution is sprayed onto a mixture of 210 g of cellulose and 70 g of lactose. A solution of 5.25 g of hydroxypropyl cellulose and 100 g of ethanol is sprayed onto the mixture whereupon it is dried and sieved. 21 g of crospovidone, 7 g of talc and 1.75 g of magnesium stearate are added and the mixture is compressed to tablets. The half-value time amounts to $T_{50}=4$ hours.

EXAMPLE 3

40 g of nifedipine are dissolved in 320 of ethanol whereupon a solution of 16 g of polyvinyl butyrale (Mowital B) and 270 g of ethanol is added. The solution thus obtained is sprayed onto a mixture of 180.8 g of cellulose and 32 g of lactose. A solution of 6 g of hydroxypropyl cellulose and 115 g of ethanol is then sprayed onto the carrier which is dried and sieved. 40 g of croscarmellose (USP XXI/N.F. XVI: cross-linked sodium carboxymethyl cellulose; disintegrating agent), 4 g of talc and 1.2 g of magnesium stearate are added. The mixture is compressed to tablets as described in Example 1 and coated, if necessary. Half-value time, $TD_{50}=5$ hours.

EXAMPLE 4

50 g of nifedipine are dissolved in 400 g of ethanol and the solution thus formed is admixed with a solution of 25 g of polyvinyl butyral and 300 g of ethanol. The solution thus obtained is sprayed onto a mixture of 232.5 g of cellulose and 50 g of lactose, whereupon a solution of 10 g of hydroxypropyl cellulose and 190 g of ethanol is sprayed onto the carrier. After drying and sieving 25 g of croscarmellose and 7.5 g of talc are added. The mixture is compressed to tablets and coated. The half-value time, $TD_{50}$ amounts 6 hours.

EXAMPLE 5

30 g of nifedipine, 30 g of polyethylene glycol 6000 (Macrogol 6000) and 3 g of polyoxy 40 stearate (Macrogol stearate) and dissolved in 240 g of ethanol and the solution thus formed is admixed with a solution of 21 g of polyvinyl butyral and 200 g of ethanol. The solution thus obtained is sprayed onto a mixture of 195 g of cellulose, 60 g of lactose and 18 g of crospovidone. After drying are sieving 5.9 g of crospovidone, 1.5 g of magnesium stearate and 0.6 g of colloidal silica are added. The mixture thus obtained is compressed to tablets and coated. $TD_{50}=4.5$ hours.

EXAMPLE 6

One proceeds as described in Example 4 except that the ethanolic solution of hydroxypropyl cellulose is divided into two parts, one half is added to the ethanolic solution of nifedipine and polyvinyl butyral before spraying while the second portion is sprayed subsequently onto the carrier.

EXAMPLE 7

8 kg of nifedipine are dissolved in 64 kg of warm ethanol, whereupon to the solution thus formed a solution of 3.2 kg of hydroxypropyl cellulose, 0.56 kg of polyvinyl butyral and 32 kg of ethanol is added. The solution thus obtained is sprayed in a fluidizing granulating equipment onto a mixture of 36.8 kg of microcrystalline cellulose, 12 kg of lactose and 2.4 kg of croscarmellose. The granules are then passed through a sieve of about 0.7 mm and dried. 8 kg of croscarmellose, 0.8 kg of talc and 0.24 kg of magnesium stearate are added and the mixture is pressed into tablets, which are convex on both sides, weigh 0.09 g and comprise 10 mg of nifedipine, with the aid of tools having a diameter of 7 mm. The tablets are coated with a film of about 4 mg based on hydroxypropyl methyl cellulose; the said layer comprises about 7.5% of yellow iron oxide pigment and about 20% of titanium dioxide.

On determining the in vitro delivery (Ph.Hg. VII "method of rotating paddle", 150 r.p.m., in 900 ml of 0.1 N hydrochloric acid, page 473) it has been found that 50% of the active ingredient is dissolved within 45–60 minutes. According to in vivo test a maximal blood level on dogs is produced after about 60 minutes [W. Vater et al.: Arzneim. Forsch. 22, 1 (1972); H. Suzuki: J. Chromatogr. 341, 341 (1985)].

EXAMPLE 8

12.00 kg of nifedipine are dissolved in 96.00 kg of a warm ethanol whereupon the solution thus formed is admixed with a solution of 5.4 kg of polyvinyl butyrale and 48.00 kg of ethanol. The solution thus obtained is sprayed onto a mixture of 54.00 kg of microcrystalline cellulose, 18.00 kg of lactose and 3.84 kg of croscarmellose in a Glatt WSG 200 fluidizing granulating equipment. Spraying rate 2.0 kg/minute, the temperature of the fluidizing air amounts to 45° C. After termination of spraying the granules are passed through an about 0.7 mm sieve on an oscillating granulating machine. The granules are returned into the container of the fluidizing granulating machine and sprayed with a solution of 1.20 kg of hydroxypropyl cellulose and 24.00 kg of ethanol. The mixture is dried in the same equipment and sieved.

In a suitable homogenizer 12.00 kg of croscarmellose, 1.20 kg of talc and 0.36 kg of magnesium stearate are admixed with the dry granules thus obtained. The mixture is either pressed into tablets weighing 0.18 g with normal concave punches having a diameter of 8 mm or filled into hard gelatine capsules. The tablets are coated with a conventional sugar-based coating. The mixture can also be filled into hard gelatine capsules whereby the wall of the capsule or the coating may preferably comprise light non-transmitting (opaque) materials in the orange region (e.g. titanium dioxide, iron oxide pigment, red or orange aluminum pigment).

According to in vitro test 50% of the active ingredient is dissolved within about 4 hours (USP XXI or Ph.Hg. VII "paddle method", 150 r.p.m).

EXAMPLE 9

500 g of nifedipine are dissolved in 4000 g of warm ethanol whereupon to the solution thus formed a solution of 50 g of hydroxypropyl cellulose, 175 g of polyvinyl butyrale and 2000 g of ethanol is added. The solution thus obtained is sprayed in a fluidizing granulating apparatus onto a mixture of 2250 g of microcrystalline cellulose, 750 g of lactose and 160 g of croscarmellose. After termination of the spraying procedure the granules are sieved lump-free and fluidizing granulation is continued by spraying a solution of 50 g of hydroxypropyl cellulose and 1000 g of ethanol onto the carrier. The granules are dried and sieved whereupon 500 g of croscarmellose, 50 g of talc and 15 g of magnesium stearate are added. The granules are compressed into lentil-form tablets which are then film-coated by applying a hydroxypropyl methylcellulose solution which comprises light non-transmitting pigments (titanium dioxide, iron oxide pigment, preferably red of orange aluminium pigment).

According to in vitro test 50% of the active ingredient are dissolved within about 2 hours (USP XXI or Ph.Hg. VII "paddle method", 150 r.p.m.).

EXAMPLE 10

110 g of nifedipine are dissolved in 880 g of ethanol under heating on a water-bath at a temperature of about 50° C. After complete dissolving a solution of 44 g of polyvinyl butyral and 720 g of ethanol are added. Into a container of a Glatt WSG 1 type fluidizing granulating equipment 498 g of microcrystalline cellulose and 88 g of lactose are introduced, fluidization is started at an inlet air temperature of 40° C. and the previously prepared solution is sprayed onto the carrier at a spraying rate of 40 ml/mixture. The pressure of the fluidizing air amounts to 0.5 bar.

During the spraying operation the temperature of the solution is maintained with the aid of a water-bath of about 50° C. In the course of this step the spraying rate of the solution is gradually increased to 50 ml/minute. Spraying is carried out for 40 minutes, the temperature of the leaving air amounts to 22°–23° C.

After applying the complete volume of liquid onto the carrier a solution of 16.5 g of hydroxypropyl cellulose and 320 g of ethanol is sprayed in. The granules thus obtained are passed through a 0.9 mm sieve and dried in the fluidizing apparatus; the temperature of the leaving air amounts to about 30° C. To the dry granules 110 g of croscarmellose, 11 g of talc and 2.75 g of magnesium stearate are added. The homogenized mixture thus obtained is compressed into tablets weighing 0.16 g and comprising 20 mg of nifedipine with the aid of a normal concave punch which has a diameter of 8 mm.

The tablets are film-coated. The coating contains titanium dioxide and reddish brown iron oxide pigment or a mixture of "Sunset yellow" and "Neococcin" aluminium pigments.

According to the test methods described in USP XXI or Ph.Hg. VII (in 0.1N hydrochloric acid, "basket-method") the tablets show the following active ingredient release:

| Time (hour) | Released nifedipine. % |
| --- | --- |
| 1 | 20 |
| 3 | 40 |
| 5 | 53 |

EXAMPLE 11

50 g of nifedipine and 75 g of polyethylene glycol 6000 (Macrogol 6000) are dissolved in 300 g of ethanol. To the solution thus formed a 12.5% solution of 200 g of Eudragit RS (see Example 1) is added. Into the container of a Uniglatt type fluidizing granulating apparatus a mixture of 150 g of lactose and 150 g of microcrystalline cellulose is introduced and the above solution is sprayed onto the carrier. The temperature of the spraying solution is adjusted to 50° C. and maintained continuously at this value with the aid of a water bath; the temperature of the fluidizing air amounts to 40° C.; spraying rate 12 g/minute. After termination of the spraying step the granules are dried in the same equipment and thereafter passed through a 0.9 mm sieve. After addition of 50 g of crospovidone (see Example 1) the mixture is homogenized and then filled into light non-transmitting (opaque) orange, red or brown hard gelatine capsules, size 2. The capsule fill weighs 0.2 g.

According to the method disclosed in USP XXI or Ph. Hg. VII the capsules show the following active ingredient release:

| Time (hours) | |
| --- | --- |
| | Released nifedipine. % |
| 1 | 22 |
| 2 | 32 |
| 3 | 41 |
| | Dissolved nifedipine. % |
| 4 | 48 |
| 5 | 54 |
| 6 | 60 |

What we claim is:

1. A process for the preparation of regulated release solid pharmaceutical compositions comprising nifedipine, as active ingredient, which comprises applying a solution or solutions containing a total of 1 part by weight of nifedipine, 0.1-1.5 parts by weight of at least one hydrophilising agent and 0.05-1.5 parts by weight of at least one retarding thus obtained and subsequently admixing the same with pharmaceutically acceptable auxiliary agents and compressing the mixture thus obtained to tablets and coating the tablets, or filling the mixture into capsules.

2. A process according to claim 1, which comprises using 0.3-1.5 parts by weight of a hydrophilising agent and 0.05-0.2 parts by weight of a retarding agent, related to 1 part by weight of nifedipine, and thus preparing a relatively quick release solid pharmaceutical composition.

3. A process according to claim 1, which comprises using 0.10-0.3 part by weight of a hydrophilising agent and 0.2-1.5 parts by weight of a retarding agent, related to 1 part by weight of nifedipine, and thus preparing a sustained release pharmaceutical solid composition.

4. A process according to claim 1, which comprises using polyethylene glycol, hydroxypropyl cellulose, polyvidone or a surfactant as hydrophilising agent.

5. A process according to any claim 1 which comprises using ethyl cellulose, polyvinyl acetate, polyvinyl butyrale or an as retarding agent.

6. A process for the preparation of regulated release solid pharmaceutical compositions comprising nifedipine as active ingredient, which comprises applying a solution or solutions containing a total of 1 part by weight of nifedipine, 0.1-1.5 parts by weight of hydroxypropyl cellulose as a hydrophilising agent and 0.05-1.5 parts by weight of polyvinyl butyral as a retarding agent onto an inert carrier, drying and sieving the product thus obtained and subsequently admixing the same with pharmaceutical auxiliary agents and compressing the mixture thus obtained to tablets and coating the tablets or filling the mixture into capsules.

7. A process according to claim 6 which comprises using as hydrophilsing agent 0.4 part by weight of hydroxypropyl cellulose and as retarding agent 0.07 part by weight of polyvinyl butyral, related to 1 part by weight of nifedipine.

8. A process according to claim 6 which comprises 0.1-0.2 part by weight of hydroxypropyl cellulose as hydrophilising agent and 0.3-0.5 part by weight of polyvinyl butyral as retarding agent, related to 1 part by weight of nifedipine.

9. A process according to claim 1, which comprises using a solution of nifedipine, a hydrophilising agent and retarding agent formed with a lower alkanol or acetone.

10. A process according to claim 6, which comprises using a solution of nifedipine, hydroxypropyl cellulose and polyvinyl butyral formed with ethanol.

11. A process according to any of claim 6, which comprises spraying a solution of nifedipine, hydroxypropyl cellulose and polyvinyl butyral in ethanol onto a solid carrier.

12. A process according to any claim 6, which comprises admixing ethanolic solutions of nifedipine, hydroxypropyl cellulose and polyvinyl butyral completely or partly and applying the resulting solution or solutions onto a solid carrier.

13. Regulated release solid pharmaceutical compositions, comprising as active ingredient nifedipine, 0.1-0.5 parts by weight of hydroxypropyl cellulose as hydrophilising agent and 0.5-1.5 parts by weight of polyvinyl butyral as retarding agent, related to 1 part by weight of nifedipine, said nifedipine, hydroxypropyl cellulose and polyvinyl butyral being coated on an inert support, the nifedipine being present in crystalline form.

14. Solid pharmaceutical composition according to claim 13, comprising 0.1-0.2 parts by weight, of hydroxypropyl cellulose as hydrophilising agent and 0.3-0.5 part by weight of polyvinyl butyral as retarding agent, related to 1 part by weight of nifedipine.

15. Regulated release solid pharmaceutical compositions prepared by the process of claim 1.

16. Regulated release solid pharmaceutical compositions, comprising as active ingredient nifedipine, 0.1-1.5 parts by weight of at least one hydrophilising agent and 0.05-1.5 parts by weight of at least one retarding agent, related to 1 part by weight of nifedipine, said nifedipine, hydrophilising agent and retarding agent being coated on an inert support, the nifedipine being present in crystalline form.

17. Relatively quick release solid pharmaceutical compositions according to claim 16 comprising 0.3-1.5 parts by weight of a hydrophilising agent and 0.05-0.2 part by weight of a retarding agent, related to 1 part by weight of nifedipine.

18. Sustained release solid pharmaceutical compositions according to claim 16 comprising 0.10–0.3 part by weight of a hydrophilising agent and 0.2–1.5 parts by weight of a retarding agent, related to 1 mole of nifedipine.

19. Solid pharmaceutical compositions according to claim 16, comprising polyethylene glycol, hydroxypropyl cellulose, polyvidone or a surfactant as hydrophilising agent.

20. Solid pharmaceutical compositions according to claim 16, comprising ethyl cellulose, polyvinyl acetate, polyvinyl butyral or an methacrylate copolymer as retarding agent.

21. Solid pharmaceutical compositions according to claim 13, comprising as hydrophilising agent 0.4 part by weight of hydroxypropyl cellulose and as retarding agent 0.07 part by weight of polyvinyl butyral, related to 1 part by weight of nifedipine.

* * * * *